United States Patent [19]
Voorhees et al.

[11] 4,181,725
[45] Jan. 1, 1980

[54] METHOD FOR ALLEVIATING PSORIASIS

[75] Inventors: John J. Voorhees, Ann Arbor, Mich.; Sven R. Hammarström, Djursholm, Sweden; Mats Å. Hamberg, Lidingö, Sweden; Bengt I. Samuelsson, Danderyd, Sweden

[73] Assignee: The Regents of the University of Michigan, Ann Arbor, Mich.

[21] Appl. No.: 793,100

[22] Filed: May 2, 1977

[51] Int. Cl.² .................. A61K 31/47; A61K 31/355; A61K 31/215; A61K 31/195
[52] U.S. Cl. ...................................... 424/258; 424/70; 424/168; 424/238; 424/284; 424/305; 424/310; 424/315; 424/317
[58] Field of Search ............... 424/284, 258, 310, 305, 424/325, 319, 317, 315, 318

[56] References Cited

U.S. PATENT DOCUMENTS

| 3,033,884 | 5/1962 | Osbond et al. | 260/413 L |
|---|---|---|---|
| 3,450,821 | 6/1969 | Cartesen et al. | 424/318 |
| 3,903,297 | 9/1975 | Robert | 424/318 |

FOREIGN PATENT DOCUMENTS 1269657  4/1972  United Kingdom ................... 424/305

OTHER PUBLICATIONS

The Merck Index, 9th Edition, 1976, pp. 183, 191, 276, 399, 463, 637, 717, 1005, 1044, 1183, 1184, 1290.

Primary Examiner—Dale R. Ore
Attorney, Agent, or Firm—Neal A. Waldrop

[57] ABSTRACT

Pharmaceutical compositions administered to humans and animals topically for treatment of proliferative skin diseases, primarily psoriasis. The composition comprises a pharmaceutical carrier with at least one active ingredient selected from the group consisting of para bromophenacyl bromide, alpha tocopherol, mepacrine, chloroquine, hydroxychloroquine, dibucaine, tetracaine, lidocaine, butacaine, procaine, ethylene diamine tetra acetic acid and ethylene glycol bis($\beta$-amino ethyl ether)-N-N' tetra acetic acid; the compositions may also include one or more unsaturated aliphatic compounds, a glucocorticoid and a prostaglandin.

12 Claims, No Drawings

METHOD FOR ALLEVIATING PSORIASIS

BRIEF DESCRIPTION OF THE INVENTION

This invention relates to pharmaceutical compositions for application to the skin and to a method for the treatment of proliferative skin diseases. The compositions may be applied topically, and the treatment can be either therapeutic or prophylactic.

DETAILED DESCRIPTION OF THE INVENTION

Proliferative skin diseases are widespread throughout the world and afflict millions of humans and their domesticated animals. This invention provides a method for treatment of such diseases and pharmaceutical compositions which are useful in alleviating them. As used hereinafter in this specification and in the claims, the expression "proliferative skin diseases" means benign and proliferative skin diseases which are characterized by epidermal cell proliferation, or division, and may also be associated with incomplete tissue differentiation. Psoriasis is the most serious of the skin diseases with which this invention is concerned. Such diseases include: psoriasis, atopic dermatities, non-specific dermatitis, primary irritant contact dermatitis, allergic contact dermatitis, lamellar ichthyosis, epidermolytic hyperkeratosis, premalignant sun induced keratosis, non-malignant keratosis, and seborrheic dermatitis in humans and atopic dermatitis and mange in domesticated animals.

Heretofore, proliferative skin diseases have been generally accepted by mankind as an ongoing evil having degrees of severity variable with time, with inherited skin traits and external factors but always have been recognized as unsightly, painful, morbid diseases. Over the history of mankind innumerable medicines and treatments have been proposed, tried and used with varying degrees of success. However, no treatment heretofor devised or pharmaceutical composition used has been entirely successful in the wide spectrum of specific diseases encompassed by the expression proliferative skin diseases.

The present day treatments of a commercial nature which are prescribed and used for the treatment of proliferative skin diseases include three approaches: (1) topical applications: coal tar derivatives, 5 fluorouracil, vitamin A acid, glucocorticoids in high dosage (constituting a non-permissive concentration), bath oils and non-specific emollient creams and ointments; (2) the systemic administration: glucocorticoids and classic anticancer agents, for example, methothrexate, hydroxyurea, azaribine, cyclophosphamide; (3) physical modalities: ultra violet light, x-irradiation, and in severe cases, surgery.

While these treatments provide, in certain cases, some remission of the original symptoms, each treatment suffers some defect, for example, temporary and incomplete mitigation of symptoms, rapid re-occurrence of the disease when mitigation is terminated, serious and sometimes irreversible damage (atrophy) resulting from the topical application for extended times of glucocorticoids, acute bone marrow suppression and cirrhosis of the liver resulting from the protracted use of methothrexate which may lead to death of the patient, and the causation of cancer by the application of anticancer drugs, x-irradiation, or ultra violet rays.

In accordance with this invention it has been found that proliferative skin diseases are alleviated, that is, the symptoms of the disease are noticeably improved or become undetectable by the treatment of the afflicted patient, or animal, with one or more of the pharmaceutical compositions described in detail hereinbelow.

For the purposes of this specification and the claims, a proliferative skin disease is alleviated when there is a noticeable decrease in the thickness of a lesion to palpation, with or without residual redness, or residual slightly dilated blood vessels or residual hyper- or hypo-pigmentation. For purposes of this invention and the claims hereof, psoriasis is alleviated when a scale-free psoriasis lesion is noticeably decreased in thickness, or noticeably but incompletely cleared or completely cleared.

The pharmaceutical compositions of this invention are effective to alleviate a proliferative skin disease when applied topically.

The term "topical" as employed herein relates to the use of the active ingredient incorporated in a suitable pharmaceutical carrier, and applied at the site of the disease for exertion of local action. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having oleaginous, absorption, water-soluble and emulsion-type bases, e.g., petrolatum, lanolin, polyethylene glycols, as well as mixtures thereof. It has been found that topical application with occlusion of an area larger than the medicated area produces improved results relative to non-occluded topical application and is, therefore, the preferred method of topical treatment with the compositions of this invention.

Certain of the compositions of this invention advantageously include skin penetrating adjuvants such as, for example, dimethyl sulfoxide, dimethyl acetamide, etc.

The best mode of practicing the process of this invention is to treat the afflicted animal, or human, so as to cause a continuing release of the active compound at the afflicted site or sites, at a selected, controlled rate which is sustained for an extended time period. Sustained release of the alleviating composition of this invention when topically applied may be accomplished by appropriate selection of a mixture of absorption adjuvants and non-absorption adjuvants to insure availability of a small proportion of the total composition applied at any instant after application and continuously until the total active compounds therein have penetrated the skin.

The compositions of this invention comprise a pharmaceutical carrier in combination with one or more compounds which are substantially non-toxic and which function in the skin of a living human or animal to modify the metabolic activity of the enzyme phospholipase A.

This invention is based on the discovery that a portion of the phospholipid component in skin cells is metabolically transformed or converted through phospholipase $A_2$ activity into abnormal quantities of arachidonic acid, prostaglandin $E_2$, prostaglandin $F_{2\alpha}$ and 12L-hydroxy-5,8,10,14-eicosatetraenoic acid. Elevated concentrations of these materials were identified in lesional epidermis of psoriasis in the Proceedings of the National Academy of Science, Volume 72, No. 12, pages 5130–5134, December 1975, in an article entitled "Increased Concentrations of Nonesterified Arachidonic Acid, 12L-Hydroxy-5,8,10,14-eicosatetraenoic Acid, Prostaglandin $E_2$, and Prostaglandin $F_2$" in "Epidermis of Psoriasis", by Sven Hammarstrom, Mats Hamberg, Bengt Samuelsson, Elizabeth A. Duell, Marek Stawiski, and John J. Voorhees.

This invention provides phospholipase $A_2$ modifier compounds which, in quantities effective to alleviate psoriasis are non-toxic, and which may be safely topically administered to a person or animal afflicted with psoriasis. The compositions of this invention comprise a pharmaceutical carrier and about 0.1% to about 20%, w/v, of at least one compound selected from the group consisting of para bromophenacyl bromide, alpha tocopherol, mepacrine, chloroquine, hydroxychloroquine, dibucaine, tetracaine, lidocaine, butacaine, procaine, ethylene diamine tetra acetic acid and ethylene glycol bis($\beta$-aminoethyl ether)-N-N' tetra acetic acid.

It is preferred to prepare topical ointments or creams containing about 10% to about 20% w/v of the selected active compound or compounds. In the case of dibucaine, tetracaine, lidocaine, butacaine, and procaine, concentrations less than about 10–15% w/v are ineffective to alleviate proliferative skin diseases as defined herein and it is preferred to employ pharmaceutical compositions containing 15–20% or in certain cases, even higher concentrations, where the selected active compound is one or more of these compounds. It is to be understood, however, that smaller quantities of one or more of these compounds are effective to enhance alleviation of a proliferative skin disease when employed in combination with one or more of the other compounds above identified, for example, in combination with hydroxychloroquine, or chloroquine, or mepacrine, or parabromophenacyl bromide, etc.

While ethylene tetra acetic acid and ethylene glycol bis($\beta$-amino ethyl ether)-N-N' tetra acetic acid are suitable for alleviating certain of the proliferative skin diseases when used alone in the amounts above stated, better results are obtained when these active compounds are used in the higher portion of the concentration range and the best results are obtained when they are incorporated in combination with one or more of the above named compounds.

The pharmaceutical compositions of this invention may include one or more of the above identified active compounds in a single topical composition such as a suspension, ointment or cream and the method of this invention may be practiced by the concurrent or sequential administration of a plurality of compositions, each of which may contain a single or a plurality of active compounds.

The compositions of this invention may be employed in conjunction with glucocorticoids. The expression "glucocorticoids" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate or triamcinolone. The glucocorticoids should be employed in minor amounts or "permissive dosage". The expression "permissive dosage" for glucocorticoids refers to a quantity which minimally supplements the natural output of adrenal cortical glycocorticoids in a normal person and which dosage administered, alone, has no perceptible effect on proliferative skin diseases.

Depending upon the severity of the proliferative skin diseases to be alleviated it has been found to be desirable to employ combinations of active compounds, at least one of which is selected from the above named group and at least one unsaturated aliphatic compound having the general formula

$$CH_3(CH_2)_m(C\equiv C-CH_2)_a(CH_2)_bCO_2H$$

wherein m is an integer from 4 to 9 inclusive, a is an integer of 2 to 5 and b is an integer of from 0 to 8, and the alkyl esters of such compounds. These compounds may be prepared by known methods, for example, by using the procedures described in U.S. Pat. No. 3,033,884 and the obvious, appropriate starting materials of the type shown therein.

Preferred unsaturated aliphatic compounds from this class include eicosa-5,8,11,14-tetraynoic acid and its alkyl esters and 5,8,11-eicosatriynoic acid and its alkyl esters. In certain cases, it is desirable to use pharmaceutical compositions containing at least one active compound for each of these groups together with a glucocorticoid preferably in a permissive dosage amount. In other cases it is desirable to include minor quantities of prostaglandins such as $PGE_1$ or $PGE_2$, particularly in those compositions containing an ingredient capable of reducing the quantity formation of $PGE_1$ or $PGE_2$ from free arachidonic acid in the skin; this does result, to some degree, in combinations containing alpha tocopherol, parabromophenacyl bromide and eicosa-5,8,11,14-tetraynoic acid. In such instances, restorative quantities of $PGE_1$ and/or $PGE_2$ are desirably included in the combination compositions, particularly for use in alleviating psoriasis.

Particularly good results are obtained from the use of compositions containing a combination of hydroxychloroquine, eicosa-5,8,11,14-tetraynoic acid and a glucocorticoid, and as above stated, for the alleviation of psoriasis, such composition may advantageously include $PGE_1$ and/or $PGE_2$. This preferred composition alleviates psoriasis best when the concentration of all active compounds totals above about 10% and preferably above about 15% w/v. Proliferative skin diseases which are less difficult to alleviate than psoriasis are alleviated by the topical application of a cream or ointment containing about 1–5% of total active compound content, and some benefit results from the use of combinations containing as little as 0.1% w/v.

Another preferred composition contains an admixture of hydroxychloroquine and 5,8,11-eicosatriynoic acid when the total concentration exceeds about 10% w/v in the topical ointment or cream; such composition may include a permissive dosage of glucocorticoid and is capable of alleviating skin proliferative diseases including psoriasis, without the addition of $PGE_1$ and/or $PGE_2$. Other advantageous combinations of active compounds include admixtures of parabromophenacyl bromide and hydroxychloroquine; parabromophenacyl bromide and chloroquine; parabromophenacyl bromide and 5,8,11-eicosa-triynoic acid; alpha tocopherol, parabromophenacyl bromide, and 5,8,11-eicosatriynoic acid; hydroxychloroquine, eicosa-5,8,11-tetraynoic acid, alpha tocopherol and $PGE_1$ or $PGE_2$.

Topical ointments can be prepared by dispersing the active compound or compounds in a suitable ointment base such as petrolatum, lanolin, polyethylene glycol, mixtures thereof, and the like. Advantageously, the active compound or compounds is finely divided by means of a colloid mill utilizing light liquid petrolatum as a levigating agent prior to dispersing in the ointment base. Topical creams and lotions are prepared by dispersing the active compound or compounds in the oil phase prior to the emulsification of the oil phase in water.

The following examples describe the manner and process of making and using the invention and set forth the best mode contemplated by the inventors of carrying out the invention, but are not to be construed as limiting.

EXAMPLE 1

| Hydroxychloroquine | 140 gm. |
|---|---|
| White petrolatum | 270 gm. |
| Cetyl alcohol | 54 gm. |
| Stearyl alcohol | 54 gm. |
| Propylene glycol | 90 gm. |
| Na lauryl sulfate | 14 gm. |
| Distilled water | 900 gm. |

The oil phase is prepared by melting the petrolatum, cetyl alcohol and stearyl alcohol together. The remaining ingredients are dissolved in the water and added to the oil phase to form a cream.

The cream is useful in the treatment of psoriasis by rubbing on the psoriatic lesions three times a day.

EXAMPLE 2

The following compositions are useful in alleviating psoriasis.

| CREAM | |
|---|---|
| Chloroquine | 210 gm. |
| White petrolatum | 270 gm. |
| Cetyl alcohol | 54 gm. |
| Stearyl alcohol | 54 gm. |
| Propylene glycol | 90 gm. |
| Na lauryl sulfate | 14 gm. |
| Distilled water | 900 gm. |

| OINTMENT | |
|---|---|
| Para bromophenacyl bromide | 12 gm. |
| Anhydrous lanolin | 18 gm. |
| Mineral oil | 25 gm. |
| White petrolatum q.s. | 100 gm. |

CREAM

One thousand grams of topical cream is prepared from the following types and amounts of ingredients:

| Hydroxychloroquine | 55 gm. |
|---|---|
| Polysorbate 80 | 50 gm. |
| Tegacid regular* | 150 gm. |
| Spermaceti | 100 gm. |
| Propylene glycol | 50 gm. |
| Methylparaben | 1 gm. |
| Deionized water q.s. | 1000 gm. |

*Self-emulsifying glyceryl monostearate from Goldschmidt Chemical Corporation, New York, N. Y.

The Tegacid and spermaceti are melted together at a temperature of 70°-80° C. The methylparaben is dissolved in about 500 gm. of water and the propylene glycol, polysorbate 80, and hydrochloroquine are added in turn, maintaining a temperature of 75°-80° C. The methylparaben mixture is added slowly to the Tegacid and spermaceti melt, with constant stirring. The addition is continued for at least 30 minutes with additional stirring until the temperature has dropped to 40°-45° C. Finally, sufficient water is added to bring the final weight to 1000 gm. and the preparation stirred to maintain homogeneity until cooled and congealed.

The composition is applied to human skin three times a day to treat psoriasis.

EXAMPLE 3

| Hydroxychloroquine | 50 gm. |
|---|---|
| Eicosa-5,8,11,14-tetraynoic acid | 50 gm. |
| $PGE_1$ | 10 gm. |
| White petrolatum | 270 gm. |
| Cetyl alcohol | 54 gm. |
| Stearyl alcohol | 54 gm. |
| Propylene glycol | 90 gm. |
| Na lauryl sulfate | 14 gm. |
| Distilled water | 900 gm. |

The oil phase is prepared by melting the petrolatum, cetyl alcohol and stearyl alcohol together. The remaining ingredients are dissolved in the water and added to the oil phase to form a cream.

The cream is useful in the treatment of psoriasis by rubbing on the psoriatic lesions three times a day.

EXAMPLE 4

| Hydroxychloroquine | 40 gm. |
|---|---|
| 5,8,11-eicosatriynoic acid | 60 gm. |
| White petrolatum | 270 gm. |
| Cetyl alcohol | 54 gm. |
| Stearyl alcohol | 54 gm. |
| Propylene glycol | 90 gm. |
| Na lauryl sulfate | 14 gm. |
| Distilled water | 900 gm. |

The oil phase is prepared by melting the petrolatum, cetyl alcohol and stearyl alcohol together. The remaining ingredients are dissolved in the water and added to the oil phase to form a cream.

The cream is useful in the treatment of psoriasis by rubbing on the psoriatic lesions three times a day.

EXAMPLE 5

| Para Bromophenacyl bromide | 40 gm. |
|---|---|
| 5,8,11-eicosatriynoic acid | 40 gm. |
| Alpha tocopherol | 5 gm. |
| White petrolatum | 270 gm. |
| Cetyl alcohol | 54 gm. |
| Stearyl alcohol | 54 gm. |
| Propylene glycol | 90 gm. |
| Na lauryl sulfate | 14 gm. |
| Distilled water | 900 gm. |

The oil phase is prepared by melting the petrolatum, cetyl alcohol and stearyl alcohol together. The remaining ingredients are dissolved in the water and added to the oil phase to form a cream.

The cream is useful in the treatment of psoriasis by rubbing on the psoriatic lesions three times a day.

EXAMPLE 6

| Hydroxychloroquine | 40 gm. |
|---|---|
| Dibucaine | 80 gm. |
| Ethylene diamine tetra acetic acid | 30 gm. |
| White petrolatum | 270 gm. |
| Cetyl alcohol | 54 gm. |
| Propylene glycol | 90 gm. |
| Na lauryl sulfate | 14 gm. |
| Distilled water | 900 gm. |

The oil phase is prepared by melting the petrolatum, cetyl alcohol and stearyl alcohol together. The remaining ingredients are dissolved in the water and added to the oil phase to form a cream.

The cream is useful in the treatment of psoriasis by rubbing on the psoriatic lesions three times a day.

EXAMPLE 7

| Mepacrine | 100 gm. |
|---|---|
| Ethylene glycol-($\beta$-amino ethyl ether)-N-N' tetra acetic acid | 80 gm. |
| White petrolatum | 270 gm. |
| Cetyl alcohol | 54 gm. |
| Stearyl alcohol | 54 gm. |
| Propylene glycol | 90 gm. |
| Na lauryl sulfate | 14 gm. |
| Distilled water | 900 gm. |

The oil phase is prepared by melting the petrolatum, cetyl alcohol and stearyl alcohol together. The remaining ingredients are dissolved in the water and added to the oil phase to form a cream.

The cream is useful in the treatment of psoriasis by rubbing on the psoriatic lesions three times a day.

The claim expression "pharmaceutical carrier" refers to the components in the above topical compositions other than the active ingredients.

What is claimed:

1. A method for alleviating psoriasis which comprises administering to the afflicted human or animal a composition containing as its active component at least one compound selected from the group consisting of para bromophenacyl bromide, alpha tocopherol, mepacrine, chloroquine, hydroxychloroquine, dibucaine, tetracaine, lidocaine, butacaine, procaine, ethylene diamine tetra acetic acid and ethylene glycol bis($\beta$-amino ethyl ether)-N-N' tetra acetic acid, said compound being in association with the pharmaceutical carrier, wherein said active component is present in an amount which is effective to alleviate psoriasis in the range of about 0.1% to about 20% w/v.

2. A method for alleviating psoriasis which comprises administering to an afflicted human or animal a composition containing hydroxychloroquine in association with a pharmaceutical carrier wherein said hydroxychloroquine is present in an amount which is effective to alleviate psoriasis in the range of about 0.1% to about 20% w/v.

3. A method for alleviating psoriasis which comprises administering to an afflicted human or animal a composition containing chloroquine in association with a pharmaceutical carrier wherein said chloroquine is present in an amount which is effective to alleviate psoriasis in the range of about 0.1% to about 20% w/v.

4. A method for alleviating psoriasis which comprises administering to an afflicted human or animal a composition containing parabromophenacyl bromide in association with a pharmaceutical carrier wherein said parabromophenacyl bromide is present in an amount which is effective to alleviate psoriasis in the range of about 0.1% to about 20% w/v.

5. A method for alleviating psoriasis which comprises administering to the afflicted human or animal a composition containing as its active component at least one compound selected from the group consisting of para bromophenacyl bromide, alpha tocopherol, mepacrine, chloroquine, hydroxychloroquine, dibucaine, tetracaine, lidocaine, butacaine, procaine, ethylene diamine tetra acetic acid and ethylene glycol bis($\beta$-amino ethyl ether)-N-N' tetra acetic acid, and at least one compound having the formula $$CH_3(CH_2)_m(C\equiv C\text{-}CH_2)_a(CH_2)_bCO_2H$$

wherein m is an integer from 4 to 9 inclusive, a is an integer of 2 to 5 and b is an integer of from 0 to 8, and the alkyl esters of such compounds, said compounds being in association with a pharmaceutical carrier wherein said compounds are present in an amount effective to alleviate psoriasis in the range of about 0.1% to about 20% w/v.

6. A method in accordance with claim 5, wherein said compounds are present in an amount between about 10% and about 20% w/v.

7. A method in accordance with claim 5, wherein said compounds present are hydroxychloroquine and eicosa-5,8,11,14-tetraynoic acid.

8. A method in accordance with claim 5, wherein said compounds are hydroxychloroquine and 5,8,11-eicosatriynoic acid.

9. A method in accordance with claim 5, wherein said compounds are parabromophenacyl bromide and hydroxychloroquine.

10. A method in accordance with claim 5, wherein said compounds are parabromophenacyl bromide and chloroquine.

11. A method in accordance with claim 5, wherein said compounds are alpha tocopherol, parabromophenacyl bromide, and 5,8,11-eicosatriynoic acid.

12. A method in accordance with claim 5, wherein said compounds are hydroxychloroquine, eicosa-5,8,11,14-tetraynoic acid, alpha tocopherol, and at least one prostaglandin selected from the group consisting of PGE$_1$ and PGE$_2$.

* * * * *